US011034742B2

United States Patent
Godaly et al.

(10) Patent No.: US 11,034,742 B2
(45) Date of Patent: Jun. 15, 2021

(54) **PEPTIDES WITH ANTIBIOTIC POTENTIAL AGAINST *MYCOBACTERIUM TUBERCULOSIS***

(71) Applicant: LINNANE PHARMA AB, Malmo (SE)

(72) Inventors: Gabriela Zuzana Victoria Godaly, Lund (SE); Erik Axel Mattias Sturegard, Lund (SE); Erik Olof Tenland, Lund (SE)

(73) Assignee: LINNANE PHARMA AB, Malmo (SE)

( * ) Notice: Subject to any disclaimer, the term of this patent is extended or adjusted under 35 U.S.C. 154(b) by 0 days.

(21) Appl. No.: 16/631,968

(22) PCT Filed: Jul. 11, 2018

(86) PCT No.: PCT/EP2018/068788
§ 371 (c)(1),
(2) Date: Jan. 17, 2020

(87) PCT Pub. No.: WO2019/016043
PCT Pub. Date: Jan. 24, 2019

(65) Prior Publication Data
US 2020/0262880 A1    Aug. 20, 2020

(30) Foreign Application Priority Data

Jul. 17, 2017 (EP) .................... 17181625
Sep. 21, 2017 (EP) .................... 17192446

(51) Int. Cl.
*C07K 14/47* (2006.01)
*A61P 31/06* (2006.01)
*A61K 38/00* (2006.01)

(52) U.S. Cl.
CPC .......... *C07K 14/4723* (2013.01); *A61P 31/06* (2018.01); *A61K 38/00* (2013.01)

(58) Field of Classification Search
None
See application file for complete search history.

(56) References Cited

U.S. PATENT DOCUMENTS

2007/0061923 A1* 3/2007 Vind ............. A61P 31/04
800/288

FOREIGN PATENT DOCUMENTS

| CN | 105198968 A | 12/2015 |
|---|---|---|
| CN | 106146629 A | 11/2016 |
| WO | 99/53053 A1 | 10/1999 |
| WO | 02/06324 A2 | 1/2002 |
| WO | 02/085934 A1 | 10/2002 |
| WO | 03/044049 A1 | 5/2003 |
| WO | 2006/050737 A1 | 5/2006 |
| WO | 2006/053565 A2 | 5/2006 |
| WO | 2006/131504 A1 | 12/2006 |
| WO | 2009/109532 A2 | 9/2009 |
| WO | 2014/001570 A1 | 1/2014 |
| WO | 2019/016043 A1 | 1/2019 |

OTHER PUBLICATIONS

International Search Report and Written Opinion for International Application No. PCT/EP2018/068788, dated Aug. 16, 2018, 12 pgs.
Baindara et al., "Laterosporulin10: a novel defensin like Class IId bacteriocin from *Brevibacillus* sp. strain SKDU10 with inhibitory activity against microbial pathogens," Microbiology, 2016, pp. 1286-1299, vol. 162.
Burbaud et al., "Trehalose Polyphleates Are Produced by a Glycolipid Biosynthetic Pathway Conserved across Phylogenetically Distant Mycobacteria," Cell Chemical Biology, 2016, pp. 278-289, vol. 23.
Linde et al., "In vitro activity of PR-39, a proline-arginine-rich peptide, against susceptible and multi-drug-resistant Mycobacterium tuberculosis," Journal of Antimicrobial Chemotherapy, 2001, pp. 575-580, vol. 47.
Marquina-Castillo et al., "Virulence, immunopathology and transmissibility of selected strains of Mycobacterium tuberculosis in a murine model," Immunology 2008, pp. 123-133, vol. 128.
Ramon-Garcia et al., "Targeting Mycobacterium tuberculosis and Other Microbial Pathogens Using Improved Synthetic Antibacterial Peptides," Antimicrobial Agents and Chemotherapy , 2013, pp. 2295-2303, vol. 57, No. 5.
Schneider et al., "Plectasin, a Fungal Defensin, Targets the Bacterial Cell Wall Precursor Lipid II," Science, 2010, pp. 168-172, vol. 328.
Schon et al., "Evaluation of wild-type MIC distributions as a tool for determination of clinical breakpoints for Mycobacterium tuberculosis," Journal of Antimicrobial Chemotherapy, 2009, pp. 786-793, vol. 64.
Snewin et al., "Assessment of Immunity to Mycobacterial Infection with Luciferase Reporter Constructs," Infection and Immunity, 1999, pp. 4586-4593, vol. 67, No. 9.
Verma et al., "Defensins: Antimicrobial peptides for therapeutic development," Biotechnology Journal, 2007, pp. 1353-1359, vol. 2.
Wimley, "Describing the Mechanism of Antimicrobial Peptide Action with the Interfacial Activity Model," ACS Chemical Biology, 2010, pp. 905-917, vol. 5.

* cited by examiner

*Primary Examiner* — Ronald T Niebauer

(57) ABSTRACT

The present invention relates to isolated variants of an antimicrobial peptide plectasin, comprising a substitution at positions 9, 13 and 32, wherein the variant has antimicrobial activity and methods for treatment of treatment of diseases mediated by *Mycobacterium tuberculosis* and gram-positive bacteria.

Figure 1:
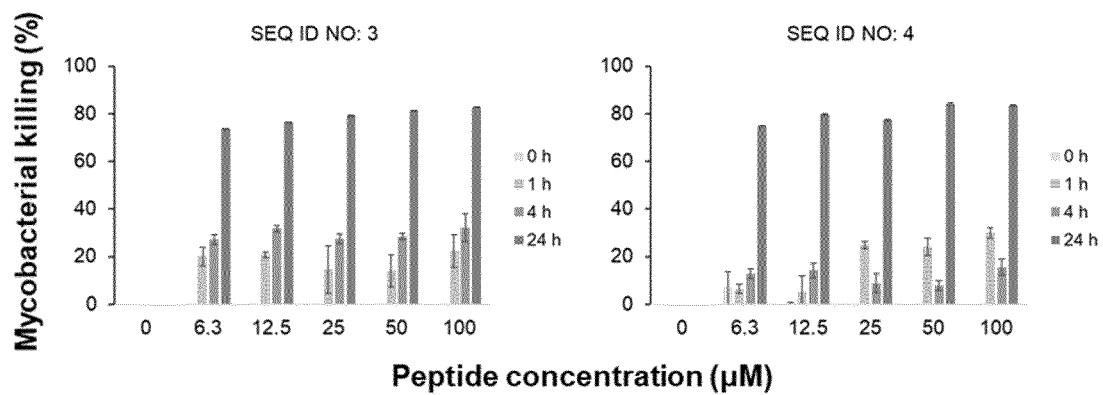
Figure 1:
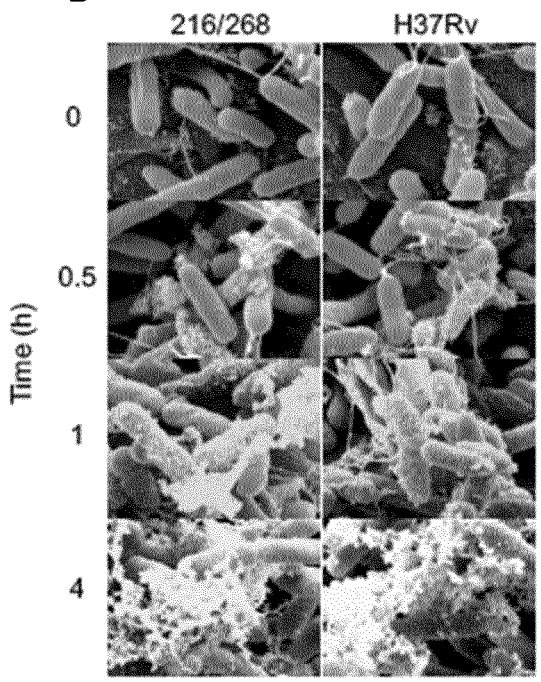
Figure 1:
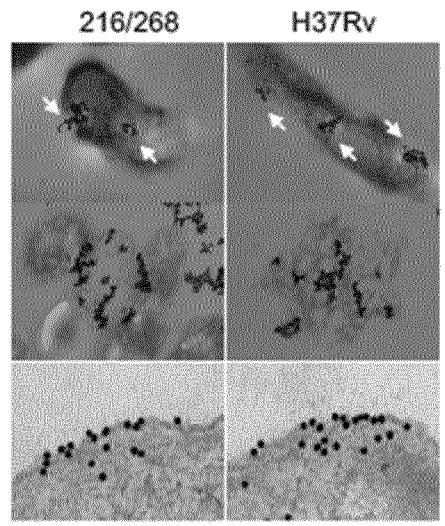

16 Claims, 5 Drawing Sheets
Specification includes a Sequence Listing.

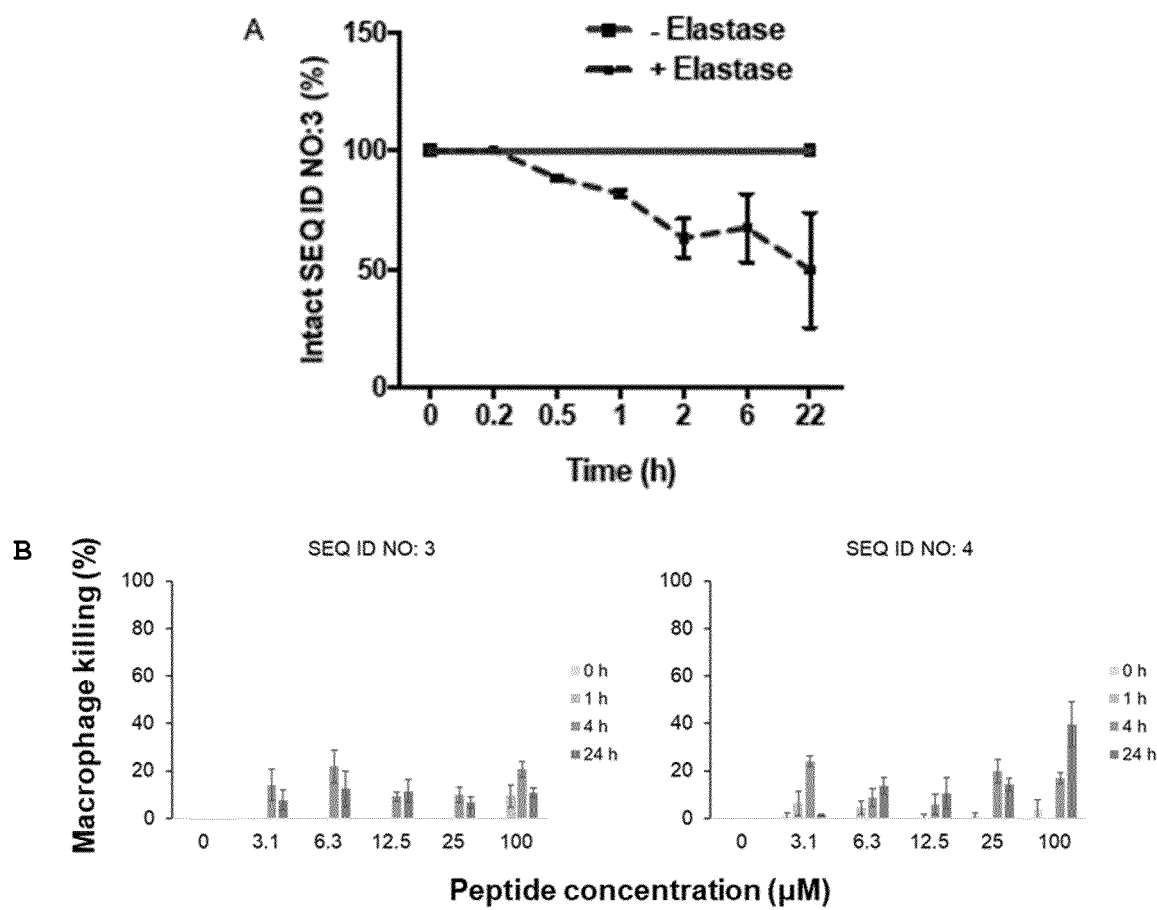

PEPTIDES WITH ANTIBIOTIC POTENTIAL AGAINST *MYCOBACTERIUM TUBERCULOSIS*

CROSS-REFERENCE TO RELATED APPLICATIONS

This application is a U.S. National Stage Application of International Application No. PCT/EP2018/068788, filed Jul. 11, 2018, which claims the benefit of, and priority to, European Patent Application No. 17181625.9, filed Jul. 17, 2017, and European Patent Application No. 17192446.7, filed Sep. 21, 2017, the entire contents of which are hereby incorporated by reference in their entirety.

INCORPORATION BY REFERENCE OF SEQUENCE LISTING

This application contains a Sequence Listing that has been submitted in ASCII format via EFS-Web and is hereby incorporated by reference in its entirety. The ASCII copy, created on Jul. 11, 2018, is named P3858PC00-SequenceListing_ST25.txt, and is 2000 bytes in size.

FIELD OF THE INVENTION

The present invention relates to novel peptides with antibiotic potential against *Mycobacterium tuberculosis* and gram-positive bacteria as well as a method for treatment of tuberculosis.

BACKGROUND OF THE INVENTION

Tuberculosis (TB) is an infectious disease primarily caused by infection with *Mycobacterium tuberculosis* (MTB). Tuberculosis is a major disease in developing countries, as well as an increasing problem in developed areas of the world. Although, the infection may be asymptomatic for a considerable period of time, the disease is most commonly manifested as an acute inflammation of the lungs, resulting in fever and a nonproductive cough but can be extra-pulmonary and spread to almost any part of the body. If untreated, serious complications and death typically result.

Treatment of tuberculosis is long and complicated, involving an intense treatment phase of two months with four antibiotic agents followed by a longer continuation phase of four months with two agents. The concept of using combinations of drugs to treat bacterial diseases was first developed to treat TB in the 1950s because single-drug therapy rapidly led to resistance. Today, isoniazid and rifampicin are standard treatment for uncomplicated infections, with a cure rate of 95% under optimal conditions. Both have superior clinical efficacy, are bactericidal and have mostly extracellular effect. However, the WHO has estimated during 2014 half a million new cases of multidrug-resistant tuberculosis (MDR-TB) strains that are resistant to rifampin and isoniazid, the two first-line TB drugs. Among the MDR-TB strains, almost 10% were extensively drug resistant (XDR) that acquired additional resistance to fluoroquinolone and to any one of the three injectable second-line anti-TB drugs amikacin, kanamycin and capreomycin. MDR- and XDR-TB requires even longer treatment with an intense treatment phase for eight months, and a continuation phase for up to 18 months. In 2012, 50% of MDR-TB and 26% of XDR-TB patients were successfully treated. Effective MDR-TB therapy is more toxic to patients than conventional treatment for drug sensitive—TB and is also more costly and prolonged. These problems are even more acute for XDR-TB patients.

While several new compounds are under investigation, alternative therapies are urgently needed both to shorten the duration of the current TB treatment and to treat MDR- and XDR-TB. Antimicrobial peptides (AMPs) have gained interest as potent candidates to develop alternative therapeutic strategy against mycobacterial infections. Many AMPs are short, cationic peptides that adopt an alpha helical conformation. Activity is dependent on a mixture of hydrophobic and cationic residues, arranged to form an amphipathic peptide. It has been proposed that the cationic portion targets the peptide to the negatively charged bacterial membrane, while the hydrophobic portion allows for intercalation into the membrane and subsequent disruption of the membrane via several proposed mechanisms (Wimley, ACS chemical biology 5, 905-917 (2010).

Many naturally occurring AMPs have been tested for activity against *M. tuberculosis*, including human and rabbit defensins and porcine protegrins. The most potent of these displayed >90% killing of *M. tuberculosis* at 50 µg/ml and acted by a mechanism that produced visible lesions on the mycobacterial outer membrane. Subsequently, some of the broadly active natural peptides were modified and tested against *M. tuberculosis* with MICs as low as 10 µM (Linde et al., The Journal of antimicrobial chemotherapy 47, 575-580 (2001). Large, entirely synthetic libraries were also tested against *M. tuberculosis* with MICs reported to be as low as 1 µM (Ramon-Garcia Antimicrobial agents and chemotherapy 57, 2295-2303 (2013). Also, the defensin, plectasin, isolated from the fungus *Pseudoplectania nigrella* and variants of plectasin have been tested against *M. tuberculosis* with MICs reported to be as low as 1.5 µg/ml (WO2009109532). None of these peptides have been reported to be active against acute *M. tuberculosis* in, in vivo models. Thus, there is a need for novel AMPs exhibiting activity against acute *M. tuberculosis* in vivo.

SUMMARY OF THE INVENTION

The present invention provides novel plectasin variants that possess direct activity against *M. tuberculosis*. These novel plectasin variants were investigated in cellular studies and one was evaluated in a murine TB model and found to inhibit hyperinflammation during acute TB infection by eliminating *M. tuberculosis*. Furthermore, the present inventors found that the plectasin variants were not toxic to human macrophages.

The solution is based on the finding, by the present inventors, that by using a previous identified plectasin variant described in WO2009109532 as SEQ ID 21, that carry a single substitution at position 9 (D9S) and further changing the methionine at position 13 to isoleucine (M13I) to avoid problems with oxidation of the molecule, and further altering the lysine at position 32, variants that exhibited strong potency against *M. tuberculosis* with very low MICs and inhibited hyperinflammation during acute TB infection by eliminating *M. tuberculosis* in mice, were identified.

Figure 3:
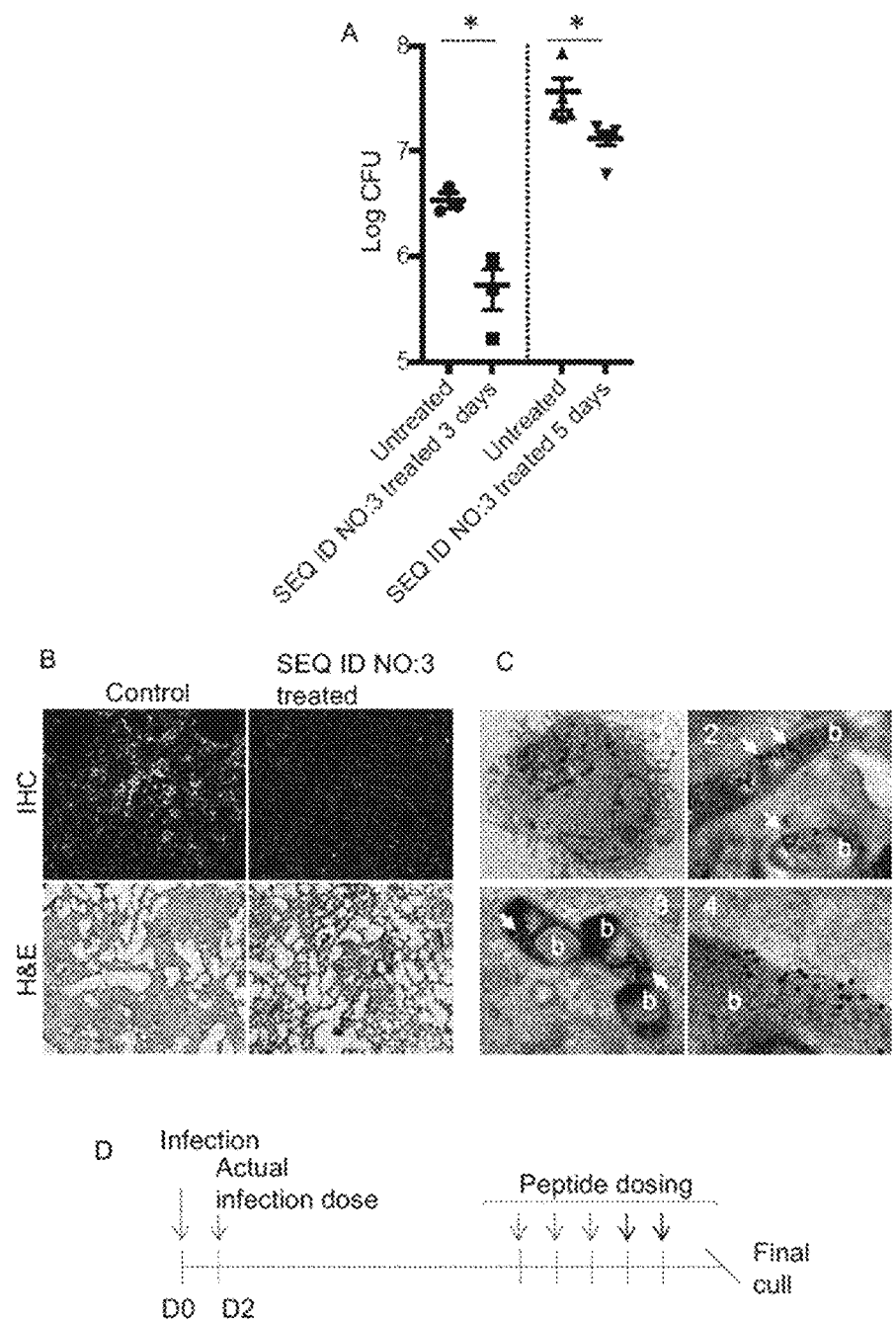
Figure 4:
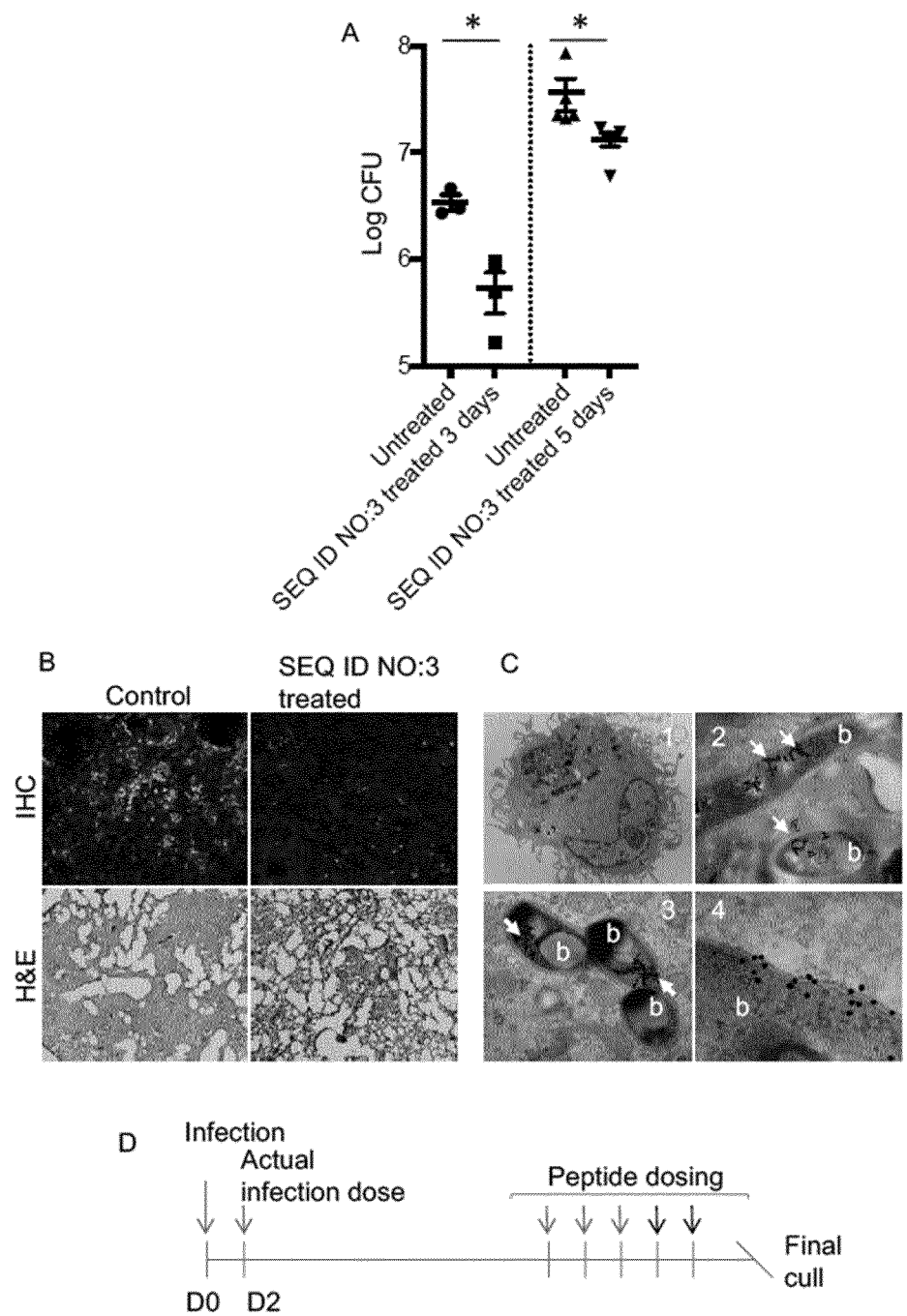

This is exemplified in working example 1 that shows that the variant antimicrobial peptides of SEQ ID NO: 3 and SEQ ID NO: 4 ruptured the mycobacterial membrane and inhibited 99% of bacterial growth at a mean concentration of 6.3 µM. Working example 5 show a significant reduction of bacterial load in mice treated with a variant antimicrobial peptide compared to the control animals. The variant antimicrobial peptide of SEQ ID NO: 3 reduced bacterial load in the lungs with 46% after three days and with 86% after five days of antimicrobial peptide treatment. Further, delivery of the variant antimicrobial peptide of SEQ ID NO: 3 during acute mycobacterial infection abrogated tissue destruction and resulted in less tissue damage, lower bacterial and neutrophil counts than infected controls. Moreover, reduced inflammation and preserved alveolar structure was further confirmed by hematoxylin and eosin staining of histologic alterations (FIG. 3). Compared to untreated mice, lung tissue of the variant antimicrobial peptide of SEQ ID NO: 3 treated mice showed reduced inflammation resembling uninfected control mice.

Thus, a first aspect of the present invention relates to an isolated variant of an antimicrobial peptide comprising the amino acid sequence of SEQ ID NO: 2, comprising a substitution at positions 9, 13 and 32, of the amino acid sequence of SEQ ID NO: 2; wherein the variant has antimicrobial activity.

A second aspect of the present invention relates to an isolated polynucleotide encoding the variant of the first aspect and/or herein relevant embodiments thereof.

A third aspect of the present invention relates to an isolated polynucleotide encoding the variant of the second aspect and/or herein relevant embodiments thereof.

A fourth aspect of the present invention relates to an expression vector comprising the polynucleotide of the third aspect and/or herein relevant embodiments thereof.

A fifth aspect of the present invention relates to a host cell comprising the polynucleotide of the fourth aspect and/or herein relevant embodiments thereof.

A sixth aspect of the present invention relates to a method of producing a variant of any of the preceding aspects and/or herein relevant embodiments thereof, comprising:
a) cultivating the host cell of the fifth aspect and/or herein relevant embodiments thereof under conditions suitable for the expression of the variant; and
b) recovering the variant.

A seventh aspect of the present invention relates a compound of the first aspects and/or herein relevant embodiments thereof for use as a medicament.

An eighth aspect of the present invention relates to a compound of the first aspects and/or herein relevant embodiments thereof for use as a medicament for treatment of diseases mediated by gram-positive bacteria; wherein the variant is capable of killing or inhibiting gram-positive bacteria.

Alternatively, may the eighth aspect be formulated as a method for treatment of diseases mediated by gram-positive bacteria in a human subject comprising administrating a therapeutic effective amount of an isolated variant of the first aspect and embodiment thereof to the human subject.

DRAWING DESCRIPTION

FIG. 1. The variant antimicrobial peptide kills *M. tuberculosis*. (A) Variant antimicrobial peptide of SEQ ID NO:3 and of the variant antimicrobial peptide of SEQ ID NO:4 were analyzed for mycobacterial killing capacity at different concentrations and time points. Data are presented as means±s.d. from three measurements.
(B) *M. tuberculosis* H37Rv and the clinical isolate TB2016/268 were treated with 6.3 μM of the variant antimicrobial peptide of SEQ ID NO: 3 and visualized by scanning electron microscopy. Membrane destabilization was observed after 30 minutes.
(C) H37RV and TB2016/268 was treated with gold-labelled the variant antimicrobial peptides of SEQ ID NO: 3 visualized with transmission electron microscopy. After one hour of treatment, the variant antimicrobial peptides of SEQ ID NO: 3 associated with the mycobacterial membrane). All experiments were repeated three times for each strain.

Figure 2:
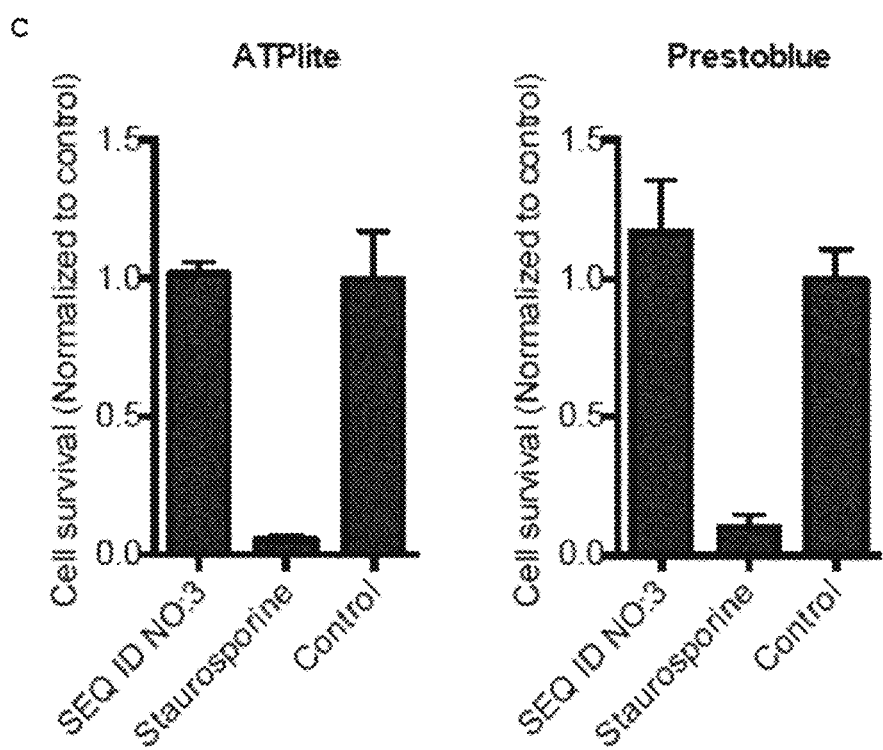

FIG. 2. The variant antimicrobial peptide resists protease degradation and is not cytotoxic (A) Human neutrophil elastase breakdown of the variant antimicrobial peptide of SEQ ID NO: 3 over time. Results are depicted as mean±95% CI of 3 independent experiments. (B) Variant antimicrobial peptide of SEQ ID NO:3 and of the variant antimicrobial peptide of SEQ ID NO:4 were analyzed for toxicity to human primary macrophages (MTT assay) at different concentrations and time points.
(C) Cytotoxicity assays of the variant antimicrobial peptide of SEQ ID NO:3 treated primary macrophages as determined by ATPlite and Prestoblue. Data are presented as means±s.d. from three measurements.

FIG. 3. Treatment efficacy of variant antimicrobial peptide. (A) Daily endotracheal treatment with the variant antimicrobial peptide of SEQ ID NO: 3 for three or five days reduced lung CFU. Results from two independent experiments (N=3 and N=5 per group) are presented as mean±sd. All P values were calculated by an unpaired Student's t-test.
(B) Representative immunohistochemistry (IHC) and eosin (H&E) staining showing lung sections from *M. tuberculosis* H37Rv infected or control mice. Neutrophil infiltration and bacteria is abundant in untreated mice. H&E staining of untreated lungs showed tissue destruction and granuloma formation. Mice treated for five days with the variant antimicrobial peptide of SEQ ID NO: 3 showed low counts of both neutrophils and bacteria in the lungs. H&E of treated lungs showed dampened destruction. Scale bars 50 μm.
(C) Lung sections from infected mice treated with gold-labelled the variant antimicrobial peptides of SEQ ID NO: 3 show peptide (arrows) around *M. tuberculosis* H37Rv (marked b) in lung macrophages.
(D) Schematic representation of experimental setup for murine pulmonary TB with *M. tuberculosis* H37Rv.

DETAILED DESCRIPTION OF THE INVENTION

The present invention relates to pharmaceuticals, and methods of using these for treatment of diseases mediated by *Mycobacterium* spp., which include variants of a parent defensin, comprising a substitution at several positions corresponding to positions 9, 13 and 32 of the mature polypeptide of SEQ ID NO: 2, wherein the variant is capable of killing or inhibiting growth of gram-positive bacteria and *Mycobacterium* such as *M. tuberculosis*.

Prior to a discussion of the detailed embodiments of the invention is provided a definition of specific terms related to the main aspects and embodiments of the invention. All terms are defined in accordance with the skilled person's normal understanding of the terms.

The term "variant" as used herein as is a polypeptide comprising an alteration, such as a substitution, insertion, and/or deletion, of one or more (several) amino acid residues at one or more (several) specific positions of the mature polypeptide of SEQ ID NO: 2. The altered polynucleotide is obtained through human intervention by modification of the polynucleotide sequence disclosed in SEQ ID NO: 1; or a homologous sequence thereof.

The term "defensin" as used herein refers to polypeptides recognized by a person skilled in the art as belonging to the defensin class of antimicrobial peptides. To determine if a polypeptide is a defensin according to the invention, the amino acid sequence is preferably compared with the hidden Markov model profiles (HMM profiles) of the PFAM database by using the freely available HMMER software package. The PFAM defensin families include Defensin_1 or "Mammalian defensin" (accession no. PF00323), Defensin_2 or "Arthropod defensin" (accession no. PF01097), Defensin_beta or "Beta Defensin" (accession no. PF0071 1), Defensin_propep or "Defensin propeptide" (accession no. PF00879) and Gamma-thionin or "Gamma-thionins family" (accession no. PF00304).

As discussed above, the first aspect of the invention relates to an isolated variant of an antimicrobial peptide comprising the amino acid sequence of SEQ ID NO: 2, comprising a substitution at positions 9, 13 and 32, of the amino acid sequence of SEQ ID NO: 2; wherein the variant has antimicrobial activity.

As known in the art, one may add one or more amino acid residues to a peptide without losing the essential activity of the peptide.

Preferably, the variant does not comprise more than 10 extra amino acid residues at the N or C-terminal ends of the sequence of SEQ ID NO: 2, more preferably the variant does not comprise more than 5 extra amino acid residues at the N or C-terminal ends of the sequence of SEQ ID NO: 2 and even more preferably the variant does not comprise more than 1 extra amino acid residue at the N or C-terminal ends of the sequence of SEQ ID NO: 2.

The defensins may belong to the alpha-defensin class, the beta-defensin class, the theta-defensin class, the insect or arthropod defensin classes, or the plant defensin class. The defensins may also be synthetic defensins sharing the characteristic features of any of the defensin classes.

Examples of such defensins include, but are not limited to, α-Defensin HNP-1 (human neutrophil peptide) HNP-2 and HNP-3; β-Defensin-12, Drosomycin, Heliomicin, γ1-purothionin, Insect defensin A, and the defensins disclosed in PCT applications WO 99/53053, WO 02/06324, WO 02/085934, WO 03/044049, WO 2006/050737 and WO 2006/053565.

The term "parent" defensin as used herein means a defensin to which a modification, e.g., substitution(s), insertion(s), deletion(s), and/or truncation(s), is made to produce the defensin variants used in the present invention. This term also refers to the polypeptide with which a variant is compared and aligned. The parent may be a naturally occurring (wild-type) polypeptide or a variant. For instance, the parent polypeptide may be a variant of a naturally occurring polypeptide, which has been modified or altered in the amino acid sequence. A parent may also be an allelic variant, which is a polypeptide encoded by any of two or more alternative forms of a gene occupying the same chromosomal locus.

The term "isolated variant" or "isolated polypeptide" as used herein refers to a variant or a polypeptide that is isolated from a source. In one aspect, the variant or polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

The term "substantially pure variant" or "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure variant or polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The variants and polypeptides of the present invention are preferably in a substantially pure form. This can be accomplished, for example, by preparing the variant or polypeptide by well-known recombinant methods or by classical purification methods. This can be accomplished, for example, by preparing the variant or polypeptide by liquid-phase or solid-phase peptide synthesis.

The term "isolated polynucleotide" as used herein, refers to amino acid sequences that are removed from their natural environment, isolated or separated, and are at least 60% free, preferably 75% free, and most preferably 95% free from other components with which they are naturally associated.

In describing the various defensin variants of the present invention, the nomenclature described below is adapted for ease of reference. In all cases, the accepted IUPAC single letter or triple letter amino acid abbreviation is employed. For an amino acid substitution, the following nomenclature is used: Original amino acid, position, substituted amino acid.

Accordingly, the substitution of threonine with alanine at position 13 is designated as "Thr13Ala" or "T13A". Multiple mutations are separated by addition marks ("+"), e.g., "Gly9Arg+Ser13Phe" or "G9R+S13F", representing mutations at positions 9 and 13 substituting glycine (G) with arginine (R), and serine (S) with phenylalanine (F), respectively.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type defensin. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

The parent defensin preferably comprises the amino acid sequence of SEQ ID NO: 2 or an allelic variant thereof. In one aspect, the parent defensin comprises the amino acid sequence of SEQ ID NO: 2. In another aspect, the parent defensin comprises the mature polypeptide of SEQ ID NO: 2. In another aspect, the parent defensin comprises amino acids 1 to 40 of SEQ ID NO: 2, or an allelic variant thereof. In another aspect, the parent defensin comprises amino acids 1 to 40 of SEQ ID NO: 2. In another aspect, the parent defensin consists of the amino acid sequence of SEQ ID NO: 2 or an allelic variant thereof. In another aspect, the parent defensin consists of the amino acid sequence of SEQ ID NO: 2. In another aspect, the parent defensin consists of the mature polypeptide of SEQ ID NO: 2. In another aspect, the parent defensin consists of amino acids 1 to 40 of SEQ ID NO: 2 or an allelic variant thereof. In another aspect, the parent defensin consists of amino acids 1 to 40 of SEQ ID NO: 2.

Variants of a parent defensin can be prepared according to any mutagenesis procedure known in the art, such as site-directed mutagenesis, synthetic gene construction, semi-synthetic gene construction, random mutagenesis, shuffling, etc. Site-directed mutagenesis is a technique in which one or several mutations are created at a defined site in a polynucleotide molecule encoding the parent defensin. The technique can be performed in vitro or in vivo.

Synthetic gene construction entails in vitro synthesis of a designed polynucleotide molecule to encode a polypeptide molecule of interest. Gene synthesis can be performed utilizing several techniques, such as the multiplex microchip-based and similar technologies wherein oligonucleotides are synthesized and assembled upon photo-programmable microfluidic chips.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent defensin and subsequent ligation of an oligonucleotide containing the mutation in the polynucleotide. Usually the restriction enzyme that digests at the plasmid and the oligonucleotide is the same, permitting sticky ends of the plasmid and insert to ligate to one another.

Site-directed mutagenesis can be accomplished in vivo by methods known in the art. Any site-directed mutagenesis procedure can be used in the present invention. There are many commercial kits available that can be used to prepare variants of a parent defensin. Single or multiple amino acid substitutions, deletions, and/or insertions can be made and tested using known methods of mutagenesis, recombination, and/or shuffling, followed by a relevant screening procedure. Mutagenesis/shuffling methods can be combined with high-throughput, automated screening methods to detect activity of cloned, mutagenized polypeptides expressed by host cells. Mutagenized DNA molecules that encode active polypeptides can be recovered from the host cells and rapidly sequenced using standard methods in the art. These methods allow the rapid determination of the importance of individual amino acid residues in a polypeptide of interest. Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide fragments may then be shuffled.

In the present invention, the isolated variants of a parent defensin comprise a substitution at one or more (several) positions corresponding to positions 9, 13 and 31 wherein the variant, is capable of killing or inhibiting growth of *M. tuberculosis*.

In one embodiment, the variant of the first aspect is a variant wherein, the substitutions are selected from the group consisting of D9A, D9E, D9F, D9G, D9H, D9I, D9K, D9L, D9N, D9P, D9Q, D9R, D9S, D9T, M13V, D9W, D9Y; M13A, M13D, M13E, M13F, M13G, M13H, M13I, M13K, M13L, M13N, M13P, M13Q, M13R, M13S, M13T, M13V, M13W, M13Y;
K32A, K32D, K32E, K32F, K32G, K32H, K32I, K32L, K32M, K32N, K32P, K32Q, K32R, K32S, M13T, K32V, K32W and K32Y.

In another embodiment, the variant of the first aspect and or any relevant embodiments thereof is a variant wherein, the substitutions are selected from the group consisting of D9N, D9S; M13A, M13D, M13E, M13F, M13G, M13H, M13I, M13K, M13L, M13N, M13P, M13Q, M13R, M13S, M13T, M13V, M13W, M13Y; K32A, K32D, K32E, K32F, K32G, K32H, K32I, K32L, K32M, K32N, K32P, K32Q, K32R, K32S, M13T, K32V, K32W and K32Y.

In a further embodiment, the variant of the first aspect and or any relevant embodiments thereof is a variant wherein, the substitutions are selected from the group consisting of D9S; M13A, M13D, M13E, M13F, M13G, M13H, M13I, M13K, M13L, M13N, M13P, M13Q, M13R, M13S, M13T, M13V, M13W, M13Y,
K32A, K32D, K32E, K32F, K32G, K32H, K32I, K32L, K32M, K32N, K32P, K32Q, K32R, K32S, M13T, K32V, K32W and K32Y.

In a still further embodiment, the variant of the first aspect and or any relevant embodiments thereof is a variant wherein, the substitutions are selected from the group consisting of D9S; M13I; K32A, K32D, K32E, K32F, K32G, K32H, K32I, K32L, K32M, K32N, K32P, K32Q, K32R, K32S, M13T, K32V, K32W and K32Y.

In a still further embodiment the variant of the first aspect is a variant wherein, the substitutions are selected from the group consisting of D9N, D9S, M13I, M13L, K32I and K32R.

In a still further embodiment the variant of the first aspect and or any relevant embodiments thereof is a variant wherein, the substitutions are selected from the group consisting of D9S, M13I, K32I and K32R.

In a still further embodiment the variant of the first aspect and or any relevant embodiments thereof is a variant wherein, the variant comprises the amino acid sequence selected from the group consisting of SEQ ID NO: 3 and SEQ ID NO: 4.

The invention relates to the use of a defensin variant of the invention for the manufacturing of a medicament for therapeutic treatment of diseases mediated by gram-positive bacteria; wherein the variant is capable of killing or inhibiting gram-positive bacteria.

Gram-positive bacteria are bacteria that give a positive result in the Gram stain test, which is traditionally used to quickly classify bacteria into two broad categories according to their cell wall. Gram-positive bacteria take up the crystal violet stain used in the test, and then appear to be purple-coloured when seen through a microscope. This is because the thick peptidoglycan layer in the bacterial cell wall retains the stain after it is washed away from the rest of the sample, in the decolorization stage of the test. Despite their thicker peptidoglycan layer, gram-positive bacteria are more receptive to antibiotics than gram-negative, due to the absence of the outer membrane.

Along with cell shape, Gram staining is a rapid method used to differentiate bacterial species. Such staining, together with growth requirement and antibiotic susceptibility testing, and other macroscopic and physiologic tests, forms the full basis for classification and subdivision of the bacteria. Based on molecular studies of the 16S sequences, twelve bacterial phyla were recognized. Two of these were both gram-positive and were divided on the proportion of the guanine and cytosine content in their DNA. The high G+C phylum was made up of the Actinobacteria and the low G+C phylum contained the Firmicutes. Actinobacteria include the *Corynebacterium, Mycobacterium, Nocardia* and *Streptomyces* genera.

*Mycobacterium* is a genus of Actinobacteria, given its own family, the Mycobacteriaceae. There are over 150 recognized species in this genus. This genus includes pathogens known to cause serious diseases in mammals, including tuberculosis (*Mycobacterium tuberculosis*) and leprosy (*Mycobacterium leprae*) in humans.

Accordingly, in one embodiment, the gram-positive bacteria are an Actinobacteria.

In a further embodiment, the Actinobacteria is a *Mycobacterium*, such as tuberculosis, preferably *M. tuberculosis*.

The defensin variants of the invention may be used as an antimicrobial veterinarian or human therapeutic or prophylactic agent. Thus, defensin variants of the invention may be used in the preparation of veterinarian or human therapeutic agents or prophylactic agents for the treatment of tuberculosis.

The defensin variants of the invention are used in an amount sufficient to kill or inhibit growth of *Mycobacterium* cells, preferably *M. tuberculosis.*

Formulations of the defensin variants of the invention are administered to a host suffering from or predisposed to a *Mycobacterium* infection, such as tuberculosis. Administration may be localized or systemic. Generally, the dose of the antimicrobial polypeptides of the invention will be sufficient to decrease the microbial population by at least about 50%, usually by at least 1 log, and may be by 2 or more logs of killing. The compounds of the present invention are administered at a dosage that reduces the microbial population while minimizing any side-effects. It is contemplated that the composition will be obtained and used under the guidance of a physician for in vivo use.

Various methods for administration may be employed. The polypeptide formulation may be given orally, or may be injected intravascularly, subcutaneously, peritoneally, by aerosol, opthalmically, intra-bladder, topically, etc. For example, methods of administration by inhalation are well-known in the art. The dosage of the therapeutic formulation will vary widely, depending on the specific antimicrobial polypeptide to be administered, the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered once or several times daily, semi-weekly, etc. to maintain an effective dosage level. In many cases, oral administration will require a higher dose than if administered intravenously. The amide bonds, as well as the amino and carboxy termini, may be modified for greater stability on oral administration. For example, the carboxy terminus may be amidated.

The compounds of this invention can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, creams, foams, solutions, suppositories, injections, inhalants, gels, microspheres, lotions, and aerosols. As such, administration of the compounds can be achieved in various ways, including oral, buccal, rectal, parenteral, intraperitoneal, intradermal, transdermal, intratracheal, etc., administration. The antimicrobial polypeptides of the invention may be systemic after administration or may be localized by the use of an implant or other formulation that acts to retain the active dose at the site of implantation.

The compounds of the present invention can be administered alone, in combination with each other, or they can be used in combination with other known compounds (e.g., perforin, anti-inflammatory agents, antibiotics, etc.) In pharmaceutical dosage forms, the compounds may be administered in the form of their pharmaceutically acceptable salts. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well known in the art. Implants are formulated as microspheres, slabs, etc. with biodegradable or non-biodegradable polymers. For example, polymers of lactic acid and/or glycolic acid form an erodible polymer that is well-tolerated by the host. The implant containing the antimicrobial polypeptides of the invention is placed in proximity to the site of infection, so that the local concentration of active agent is increased relative to the rest of the body. The term “unit dosage form”, as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the unit dosage forms of the present invention depend on the compound employed and the effect to be achieved, and the pharmacodynamics associated with the compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from 0.1 pg to 100 mg per kg weight of subject per administration. A typical dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

The use of liposomes as a delivery vehicle is one method of interest. The liposomes fuse with the cells of the target site and deliver the contents of the lumen intracellular. The liposomes are maintained in contact with the cells for sufficient time for fusion, using various means to maintain contact, such as isolation, binding agents, and the like. In one aspect of the invention, liposomes are designed to be aerosolized for pulmonary administration. Liposomes may be prepared with purified proteins or peptides that mediate fusion of membranes, such as Sendai virus or influenza virus, etc. The lipids may be any useful combination of known liposome forming lipids, including cationic or zwitterionic lipids, such as phosphatidylcholine. The remaining lipid will normally be neutral or acidic lipids, such as cholesterol, phosphatidyl serine, phosphatidyl glycerol, and the like.

For use in the subject methods, the antimicrobial polypeptides of the invention may be formulated with other pharmaceutically active agents, particularly other antimicrobial agents. Other agents of interest include a wide variety of antibiotics, as known in the art. Classes of antibiotics include penicillins, e.g. penicillin G, penicillin V, methicillin, oxacillin, carbenicillin, nafcillin, ampicillin, etc.; penicillins in combination with beta-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; fluoroquinolones; chloramphenicol; metronidazole; spectinomycin; trimethoprim; vancomycin; etc.

Anti-mycotic agents are also useful, including polyenes, e.g. amphotericin B, nystatin; 5-flucosyn; and azoles, e.g. miconazol, ketoconazol, itraconazol and fluconazol. Antituberculotic drugs include isoniazid, ethambutol, streptomycin, pyrazinamide and rifampin. Cytokines may also be included in a formulation of the antimicrobial polypeptides of the invention, e.g. interferon gamma, tumor necrosis factor alpha, interleukin 12, etc.

The polypeptides of the invention may be prepared by in vitro synthesis, using conventional methods as known in the art. Various commercial synthetic apparatuses are available, for example automated synthesizers by Applied Biosystems Inc., Beckman, etc. By using synthesizers, naturally occurring amino acids may be substituted with unnatural amino acids, particularly D-isomers (or D-forms) e.g. D-alanine and D-isoleucine, diastereoisomers, side chains having different lengths or functionalities, and the like. The sequence and the manner of preparation will be determined by convenience, economics, purity required, and the like.

Chemical linking may be provided to various peptides or proteins comprising convenient functionalities for bonding, such as amino groups for amide or substituted amine formation, e.g. reductive amination, thiol groups for thioether or disulfide formation, carboxyl groups for amide formation, and the like.

If desired, various groups may be introduced into the peptide during synthesis or during expression, which allow for linking to other molecules or to a surface. Thus, cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein In one embodiment, the variant of the first aspect and or any relevant embodiments thereof is a variant produced by in vitro synthesis.

EXAMPLES

The following examples are merely illustrative of the present invention and should not be construed as limiting the scope of the invention in any way as many variations and equivalents that are encompassed by the present invention will become apparent to those skilled in the art upon reading the present disclosure.

Methods.

Peptide

Peptides were manufactured by solid phase peptide synthesis, followed by cyclisation of the three disulphide bonds and purification by sequential chromatography steps (PolyPeptide Laboratories AB, Limhamn, Sweden). The purity (>90%) of the peptide was confirmed by high-pressure liquid chromatography.

Bacteria

For screening experiments, *Mycobacterium bovis bacillus* Calmette-Guerin (BCG) Montreal strain containing the pSMT1-luxAB plasmid was prepared as previously described in Snewin et al, Infection and immunity 67, 4586-4593 (1999). Briefly, the mycobacteria were grown in Middlebrook 7H9 broth, supplemented with 10% ADC enrichment (Becton Dickinson, Oxford, UK) and hygromycin (50 mg/L; Roche, Lewes, UK), the culture was washed twice with sterile PBS, and re-suspended in broth and then dispensed into vials. Glycerol was added to a final concentration of 25% and the vials were frozen at −80° C. Prior to each experiment, a vial was defrosted, added to 9 ml of 7H9/ADC/hygromycin medium, and incubated with shaking for 72 h at 37° C. Mycobacteria were then centrifuged for 10 minutes at 3000× g, washed twice with PBS, and re-suspended in 10 ml of PBS.

For murine TB experiments, we obtained a lipid-modified *M. tuberculosis* H37Rv for increased virulence (Burbaud, S., et al. Cell Chem Biol 23, 278-289 (2016), from Christophe Guilhot at the Institut de Pharmacologie et de Biologie Structurale (IPBS), Toulouse, France, was grown to mid-log phase in Middlebrook 7H9 culture medium, supplemented with 0.05% Tween 80, 0.2% glycerol and 10% oleic acid-albumin-dextrose-catalase (OADC) enrichment (Becton Dickinson, Oxford, UK).

In preparation for MIC-determination and electron microscopy studies of the effect of the variant antimicrobial peptides on *M. tuberculosis* in vitro, H37Rv (ATCC 27294) and a clinical strain isolated from pleural effusion (TB2016/268) were cultured in MGIT960 according to manufacturer's instructions. Both strains were fully susceptible to first-line antibiotics and were verified to be *M. tuberculosis* using standard methods at Clinical Microbiology, Lund, Sweden.

Antibacterial In Vitro Activity Studies

To measure peptide activity against mycobacteria, BCG was diluted in Middlebrook 7H9 medium (104 CFU; 150 µL/well) in 96-well opaque white plates (Corning). Peptides (0, 6.3, 12.5, 25, 50 or 100 µM) were added to the wells. Growth controls containing no peptide and peptide without bacteria were also prepared. The plates were incubated at 37° C. for up to 24 hours before adding 0.1% n-decyl aldehyde (Decanal, Sigma), a substrate for bacterial luciferase. Bioluminescence was measured for 1s using a TriStar microplate reader (Berthold Technologies).

Scanning Electron Microscopy (SEM)

The effect of peptide on *M. tuberculosis* H37Rv and the clinical isolate was determined by SEM. Bacteria was grown to $10 \times 10^8$ CFU and treated with the variant antimicrobial peptide of SEQ ID NO: 3 (6.3 µM) for 0, 0.5, 1, 2, 4 or 24 h. Bacteria were then pelleted at 3,000×g for 7 min, suspended in fixation solution (4% formaldehyde and 2.5% glutaraldehyde in sodium cacodylate), and absorbed onto poly-L-lysine-coated glass coverslips for 1 h. Samples were processed as previously described (22) and examined in a Philips/FEI XL30 FEG scanning electron microscope at an acceleration voltage of 5 kV and a working distance of 10 mm.

MIC

To assess the variant antimicrobial peptides of SEQ ID NO: 3 and SEQ ID NO: 4 for anti-mycobacterial activity we measured the minimal inhibitory concentration (MIC) against two strains of *M. tuberculosis* (H37Rv and TB2016/268) using the MGIT 960-culture system (BACTEC MGIT 960, Becton Dickinson, Franklin Lakes, N.J., USA) following previously validated methods. In brief, the variant antimicrobial peptides diluted in PBS were added to MGIT960-culture tubes in increasing $\log_2$-concentrations. Bacteria in log phase were added to the MGIT960-tubes medium and the lowest the variant antimicrobial peptide concentration with no detected growth was determined as the MIC using a MGIT-tube with bacteria diluted 1:100 as growth control. The MIC-determinations for both strains were performed twice on separate occasions.

Transmission Electron Microscopy

For transmission electron microscopy (TEM) and visualization of peptide effects on bacteria, *M. tuberculosis* H37Rv and the clinical isolate ($1-2 \times 10^6$ cfu/sample) were incubated for 0, 0.5, 1, 4 or 24 h at 37° C. with the variant antimicrobial peptide of SEQ ID NO: 3 (6.3 µM). Bacterial samples were adsorbed onto carbon-coated copper grids for 2 min, washed briefly with two drops of water, and negatively stained with two drops of 0.75% uranyl formate. The grids were rendered hydrophilic by glow discharge at low pressure in air. All samples were examined with a Jeol JEM 1230 electron microscope operated at 80 kV accelerating voltage. Images were recorded with a Gatan Multiscan 791 charge-coupled device camera.

Protease Sensitivity Assay

The variant antimicrobial peptide of SEQ ID NO: 3 (1 µg) was incubated at 37° C. with human neutrophil elastase (HNE, 0.4 µg, 29 units/mg; Calbiochem (La Jolla, Calif.), Cathepsin G (0.4 µg, EMD Millipore) and human α-thrombin (0.4 µg Innovative Research) in a total volume of 20 µL for 6 h. Furthermore 2 µg of the variant antimicrobial peptide of SEQ ID NO: 3 was incubated with 0.4 µg of HNE for kinetic study of peptide degradations. The materials were analyzed on 10-20% precast SDS-PAGE Tris-Tricine gels (Life Technologies) and analyzed after staining with Coomassie Blue R-250. The materials were analyzed on 10-20% precast SDS-PAGE Tris-Tricine gels (Life Technologies) and analyzed after staining with Coomassie Blue R-250.

Primary Human Macrophages

Human venous blood mononuclear cells were obtained from healthy volunteers using a Lymphoprep density gradient (Axis-Shield, Oslo, Norway) according to the manufacturers instructions. To obtain pure monocytes, the cell suspension was applied to CD14 micro beads (MACS), washed and passed through magnetic column according to manufacturers description. The monocytes were counted (Sysmex), diluted in RPMI medium containing GM-CSF (50 ng/mL) and seeded in 96-well plates ($10^5$/well) for a week to differentiate into macrophages.

Cytotoxicity Assays

Primary macrophages were prepared from whole blood (see above). The medium was replaced with fresh medium containing 0, 6.3, 12.5, 25 or 100 µM peptides and incubated for 0, 1, 4 and 24 h in 5% $CO_2$ atmosphere. For cytotoxicity measurement, 10 µl 3-(4,5-dimethylthiazol-2-yl)-2,5 diphenyltetrazolium bromide (MTT) solution (Sigma) was added to each well according to manufacturers instructions, and analyzed in a spectrophotometer at 580 nm.

The variant antimicrobial peptide of SEQ ID NO: 3 cytotoxicity was further examined by PrestoBlue® and ATPlite™ assays. Primary macrophages were treated with 100 µM variant antimicrobial peptide of SEQ ID NO: 3 or 50 µM Staurosporine (S-4400, Sigma) for 24 hours. Cell viability was assessed with PrestoBlue® fluorescence (A13261, Thermo Scientific) and cellular ATP levels using ATPlite™ kit (#6016943, Perkin Elmer) compared to untreated control, according to the manufacturers' instructions.

Infection of Mice with *M. tuberculosis*

All animal procedures were performed under the license issued by the UK Home Office and in accordance with the Animal Scientific Procedures Act of 1986. Six to eight week old female BALB/c mice (Charles River Ltd, UK) were maintained in biosafety containment level 3 (BSL3) facilities at the Centre for Molecular Microbiology and Infection, Imperial College London, London, United Kingdom according to institutional protocols. Mice were infected with approximately $7 \times 10^3$ CFU/ml of *M. tuberculosis* H37Rv via the intranasal route (control group, n=8 and the variant antimicrobial peptide of SEQ ID NO: 3 group, n=5). Two days after infection, 3 control mice were euthanized to determine the actual infectious dose in the lungs. Following 16 (experiment 1) or 21 (experiment 2) days of infection, the variant antimicrobial peptide of SEQ ID NO: 3 group were treated for 3 (experiment 1) or 5 (experiment 2) consecutive days with 0.83 mg variant antimicrobial peptide diluted in 50 µL PBS by intra-tracheal administration. The control groups received 50 µL PBS by intra-tracheal administration. An extra group (n=5) in experiment 1 was treated with gold-labelled variant antimicrobial peptide for three days. Following treatment, mice were culled and lungs and spleen were aseptically removed and the left lung lobe placed for 24 hours in 10% buffered formalin, for later histology. The remaining tissues were homogenized in PBS containing 0.05% Tween-80, serially diluted and plated on Middlebrook 7H11 agar plates supplemented with 0.5% glycerol and 10% OADC. The number of colony forming units (CFU) from all mice was enumerated 21 days later.

Histology and Immunohistochemistry

Formalin fixed tissue was transferred to 70% ethanol overnight, then embedded and frozen in optimal cutting temperature compound (Sakura Finetek USA) for cryosectioning (8 µm; Leica microtome). Section were collected on positively charged microscope slides (Superfrost/Plus, Thermo Fisher Scientific), fixed in acetone-methanol (1:1, 10 min), dried, permeabilized (0.2% Triton X-100, 5% normal goat serum/PBS), and stained with primary rat anti-neutrophil antibody (NIMP-R14) (1:200; Abcam, ab2557), rabbit monoclonal anti—*M. tuberculosis* antibody (1:100; Lionex, NB200-579) and mouse anti-neutrophil (1:50; Abcam, ab119352), followed by Alexa 488 or Alexa 568—labelled rabbit anti-rat or goat anti-mouse immunoglobulin G secondary antibodies (Molecular Probes; A-21210, A-11001, and A-11011). Nuclei were counterstained with DAPI (4',6-diamidino-2-phenylindole) (0.05 mM; Sigma-Aldrich). Slides were examined by fluorescence microscopy (AX60, Olympus Optical). Richard-Allan Scientific Signature Series Hematoxylin 7211 and Eosin-Y 7111 (Thermo Scientific) were used to counterstain the tissue sections.

Statistical Analysis

Graphs and statistics were generated using the Prism software (GraphPad Software, version 6.1). Significance, where indicated, was calculated using the unpaired Student's t-test. Significance was accepted at *$p<0.05$, $p<0.01$, or *$p<0.001$.

Study Approval

The Local Ethical Review Board Dnr 2011/403 and 2014/35 approved the donation of blood from human volunteers for the in vitro studies (Lund, Sweden), and the animal studies have been approved (PPL 70/7160) by the Local Animal Welfare and Ethical Review Board (London, UK).

Results.

Example 1

Variant Antimicrobial Peptides Kill *M. tuberculosis*

The variant antimicrobial peptide precursor, plectasin, contains a cysteine-stabilized α-helix/β-sheet motif (CSαβ) that interferes with peptidoglycan precursor to induce lysis. *M. tuberculosis* H37Rv and clinical isolate TB2016/268 were treated with up to 100 µM of variant antimicrobial peptides of SEQ ID NO: 3 and SEQ ID NO: 4. Results showed that variant antimicrobial peptide of SEQ ID NO: 3 resulted in Mycobacterial killing efficiency of 73.8%±(0.1), where as variant antimicrobial peptide of SEQ ID NO: 4 resulted in Mycobacterial killing efficiency of 74.8%±(0.1), both at 6.3 µM peptide concentration (FIG. 1A).

Scanning electron microscopy showed membrane disruption starting at 30 minutes (FIG. 1B). The median and range of MIC for the two strains were 6.3 µM (6.3-12.5) for H37Rv and 6.3 µM (3.1-6.3) for TB2016/268, respectively.

The variant antimicrobial peptide of SEQ ID NO: 3 inhibited the bacteria at concentrations comparable with standard drugs targeting *M. tuberculosis* such as rifampicin, isoniazid, ethambutol and ofloxacin (table 1).

TABLE 1

Minimal inhibitory concentration (MIC) distributions

| Drug | Molecular weight (g/mol) | MIC (µM) | MIC (mg/L) |
|---|---|---|---|
| Rifampicin | 822.94 | 1.2* | 1.0* |
| Isoniazid | 137.14 | 1.5* | 0.2* |
| Ethambutol | 204.31 | 24.5* | 5.0* |
| SEQ ID NO: 3 | 4383.89 | 6.8 | 27.5 |

*Schon, T., et al. The Journal of Antimicrobial Chemotherapy 64, 786-793 (2009)

Example 2

The Variant Antimicrobial Peptide Interferes with Mycobacterial Membrane

Plectasin was previously shown to interact differently with membranes compared to other AMPs, binding directly to the cell-wall precursor Lipid II (Schneider, T., et al. Science 328, 1168-1172 (2010). Lipid II is also a major constituent of cell-wall building block in mycobacterial spp, suggesting that the variant antimicrobial peptide of SEQ ID NO: 3, with 93% as similarity to plectasin, could possess a similar binding action. We labelled the variant antimicrobial peptide of SEQ ID NO: 3 with gold and studied with TEM. We observed that the variant antimicrobial peptide of SEQ ID NO: 3 associated with the mycobacterial envelope within one hour of exposure and disrupted bacterial membranes (FIG. 10).

Example 3

The Variant Antimicrobial Peptide of SEQ ID NO: 3 is Resistant to Degradation by Proteases A major barrier limiting the clinical application of AMPs is their susceptibility to protease degradation, such as the neutrophil elastase, in biological fluids. Also, bacteria produce a variety of proteases to protect themselves from peptides. To investigate whether the variant antimicrobial peptide of SEQ ID NO: 3 is degraded by proteases, the peptide was incubated with Human neutrophil elastase (HNE), Cathepsin G and human α-thrombin. Of the investigated proteases, only HNE showed peptide degradation, with approximately 50 breakdown after 22 hours (FIG. 2A).

Example 4

Variant Antimicrobial Peptides of SEQ ID NO: 3 and SEQ ID NO: 4 are not Toxic to Human Cells Several AMPs have been reported as toxic in vitro. We investigated if the variant antimicrobial peptide of SEQ ID NO: 3 and SEQ ID NO: 4 showed cytotoxic effects on primary human macrophages. In one experiment, cells were incubated with 0, 6.3, 12.5, 25 or 100 µM peptides for 0, 1, 4 and 24 h. After adding MTT, analysis of the samples showed that variant antimicrobial peptide of SEQ ID NO: 3 resulted in a macrophage viability of 87.5%±(7.4), where as variant antimicrobial peptide of SEQ ID NO: 4 resulted in a macrophage viability of 86.3%±(3.6), both at 6.3 µM peptide concentration (FIG. (2B). In another experiment, cells were treated with 100 µM of the variant antimicrobial peptide of SEQ ID NO: 3 or 50 µM Staurosporine (positive control) for 24 hours. Cellular ATP levels and reducing metabolites were measured using ATPlite and PrestoBlue, respectively. The variant antimicrobial peptide of SEQ ID NO: 3 did not show any toxicity on primary human macrophages in either measurement (FIG. 2C).

Example 5

Treatment Efficacy of Variant Antimicrobial Peptide of SEQ ID NO: 3 in Mice with *M. tuberculosis* Infection Two bactericidal activity experiments were performed in a murine TB model with *M. tuberculosis* H37Rv, comparing two dosing protocols (Marquina-Castillo, B., et al. Immunology 128, 123-133 (2009) (FIG. 3D). In the first experiment, the animals received three doses of the variant antimicrobial peptide of SEQ ID NO: 3, while the dosing was increased to five days in the second experiment. In both experiments we observed a significant CFU reduction by 46% after three days (p=0.0137) and by 86% after five days (p=0.0262) in the mice treated with the variant antimicrobial peptide of SEQ ID NO: 3 compared to the control animals (FIG. 3A). With TEM we could demonstrate that gold-labelled variant antimicrobial peptide of SEQ ID NO: 3 targets *M. tuberculosis* within macrophages in lung sections from infected mice (FIG. 3C).

Example 6

Variant Antimicrobial Peptide of SEQ ID NO: 3 Attenuates Inflammation During Acute Tuberculosis The variant antimicrobial peptide of SEQ ID NO: 3 treatment abrogated tissue destruction in infected mice as shown by immunohistochemistry (FIG. 3C). Lung tissue sections from the variant antimicrobial peptide of SEQ ID NO: 3 treated *M. tuberculosis* infected mice showed less tissue damage, lower bacterial and neutrophil counts than infected controls. Reduced inflammation and preserved alveolar structure was further confirmed by hematoxylin and eosin staining, which showed cellular infiltrates and consolidation of the lung in untreated lungs, both of which were missing from the lungs of the variant antimicrobial peptide of SEQ ID NO: 3 treated animals (FIG. 3B).

CONCLUSIONS

The present invention has identified variants of the plectasin peptide from *P. nigrella* that kills *M. tuberculosis* at antibiotic concentrations. It was shown that the variant antimicrobial peptide of SEQ ID NO: 3 and SEQ ID NO: 4 inhibits *M. tuberculosis*. *M. tuberculosis* was treated with 6.3 uM of variant antimicrobial peptides of SEQ ID NO: 3 and SEQ ID NO: 4 and it was found that variant antimicrobial peptide of SEQ ID NO: 3 resulted in Mycobacterial killing efficiency of 73.8%±(0.1) and a cytotoxicity of 87.5%±(7.4) where as variant antimicrobial peptide of SEQ ID NO: 4 resulted in Mycobacterial killing efficiency of 74.8%±(0.1) and a cytotoxicity of 86.3%±(3.6). Moreover, it was observed that variant antimicrobial peptide of SEQ ID NO: 3 kills *M. tuberculosis* at antibiotic concentrations comparable with standard drugs targeting *M. tuberculosis* such as rifampicin, isoniazid, ethambutol and ofloxacin (Table 1).

Results from a murine model of acute TB supported these observations, as the concentration of administered drug was comparable to daily dosage of rifampicin in adult human TB patients. We observed that the variant antimicrobial peptide of SEQ ID NO: 3 effectively eliminated *M. tuberculosis* in a murine TB model. The peptide could reduce bacterial load in the lungs with 46% after three days and with 86% after five days of treatment. At the same time, it was observed that the inflammatory response was markedly down-modulated.

Peptides are generally easily degradable, even though administration to nasal and pulmonary compartments induces relatively low proteolytic activity. These compartments are also highly vascularized and have large absorptive surfaces especially in the lungs resulting in improved absorption. We observed that the variant antimicrobial peptide of SEQ ID NO: 3 was not degraded by proteases and we could find intact peptide in lung tissue macrophages after therapeutic treatment of the mice. Further, it was observed that the inflammatory response was dampened markedly.

REFERENCE LIST

1. Wimley, ACS Chemical Biology 5, 905-917 (2010).
2. Linde et al., The Journal of Antimicrobial Chemotherapy 47, 575-580 (2001).
3. Ramon-Garcia, Antimicrobial Agents and Chemotherapy 57, 2295-2303 (2013).
4. Snewin et al., Infection and Immunity 67, 4586-4593 (1999).
5. Burbaud, S., et al. Cell Chemical Biology 23, 278-289 (2016).
6. Schon, T., et al. The Journal of Antimicrobial Chemotherapy 64, 786-793 (2009).

The invention claimed is:

1. An isolated variant of an antimicrobial peptide comprising the amino acid sequence of SEQ ID NO: 2 and comprising a substitution at positions 9, 13 and 32 of the amino acid sequence of SEQ ID NO: 2; wherein the variant has antimicrobial activity.

2. The variant of claim 1, wherein the substitution at position 9 is selected from the group consisting of D9A, D9E, D9F, D9G, D9H, D9I, D9K, D9L, D9N, D9P, D9Q, D9R, D9S, D9T, D9W, and D9Y;

the substitution at position 13 is selected from the group consisting of M13A, M13D, M13E, M13F, M13G, M13H, M13I, M13K, M13L, M13N, M13P, M13Q, M13R, M13S, M13T, M13V, M13W, and M13Y; and the substitution at position 32 is selected from the group consisting of K32A, K32D, K32E, K32F, K32G, K32H, K32I, K32L, K32M, K32N, K32P, K32O, K32R, K32S, K32V, K32W, and K32Y.

3. The variant of claim 2, wherein the substitutions are selected from the group consisting of D9N, D9S, M13I, M13L, K32I and K32R.

4. The variant of claim 2, wherein the substitutions are selected from the group consisting of D9S, M13I, K32I and K32R.

5. The variant of claim 1, wherein the variant comprises the amino acid sequence selected from the group consisting of SEQ ID NO: 3 and SEQ ID NO: 4.

6. An isolated polynucleotide encoding the variant of claim 1.

7. A nucleic acid construct comprising the polynucleotide of claim 6.

8. An expression vector comprising the polynucleotide of claim 6.

9. A host cell comprising the polynucleotide of claim 6.

10. A method of producing the variant of claim 1, comprising:
   a) cultivating a host cell comprising a polynucleotide encoding the variant of claim 1 under conditions suitable for the expression of the variant; and
   b) recovering the variant.

11. A method for treating a disease mediated by gram-positive bacteria, the method comprising administering the variant of claim 1 to a subject in need thereof.

12. The method of claim 11, wherein the variant is capable of killing or inhibiting the gram-positive bacteria.

13. The method of claim 12, wherein the gram-positive bacteria are an Actinobacteria.

14. The method of claim 13, wherein the Actinobacteria is a *Mycobacterium*.

15. The method of claim 14, wherein the Actinobacteria is *Mycobacterium tuberculosis*.

16. The method of claim 11 wherein the subject is a human.

* * * * *

UNITED STATES PATENT AND TRADEMARK OFFICE
CERTIFICATE OF CORRECTION

PATENT NO. : 11,034,742 B2
APPLICATION NO. : 16/631968
DATED : June 15, 2021
INVENTOR(S) : Gabriela Zuzana Victoria Godaly et al.

Page 1 of 1

It is certified that error appears in the above-identified patent and that said Letters Patent is hereby corrected as shown below:

In the Claims

Column 20, Line 51 (Claim 2): "K320" should read --K32Q--

Signed and Sealed this
Fifth Day of October, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 4

<210> SEQ ID NO 1
<211> LENGTH: 120
<212> TYPE: DNA
<213> ORGANISM: Artificial Sequence
<220> FEATURE:
<223> OTHER INFORMATION: SYNTHESIZED

<400> SEQUENCE: 1

```
ggatttggat gcaatggtcc ttgggatgag gatgatatgc agtgccacaa tcactgcaag      60
tctattaagg gttacaaggg aggttattgt gctaagggg gctttgtttg caagtgttac     120
```

```
<210> SEQ ID NO 2
<211> LENGTH: 40
<212> TYPE: PRT
<213> ORGANISM: Artificial Sequence
<220> FEATURE:
<223> OTHER INFORMATION: SYNTHESIZED

<400> SEQUENCE: 2

Gly Phe Gly Cys Asn Gly Pro Trp Asp Glu Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40

<210> SEQ ID NO 3
<211> LENGTH: 40
<212> TYPE: PRT
<213> ORGANISM: Artificial Sequence
<220> FEATURE:
<223> OTHER INFORMATION: SYNTHESIZED

<400> SEQUENCE: 3

Gly Phe Gly Cys Asn Gly Pro Trp Ser Glu Asp Ile Gln Cys His
1               5                   10                  15

Asn His Cys Lys Ser Ile Lys Gly Tyr Lys Gly Gly Tyr Cys Ala Arg
            20                  25                  30

Gly Gly Phe Val Cys Lys Cys Tyr
        35                  40

<210> SEQ ID NO 4
<211> LENGTH: 40
<212> TYPE: PRT
<213> ORGANISM: Artificial Sequence
<220> FEATURE:
<223> OTHER INFORMATION: SYNTHESIZED

<400> SEQUENCE: 4

Gly Phe Gly Cys Asn Gly Pro Trp Ser Glu Asp Ile Gln Cys His
1               5                   10                  15

Asn His Cys Lys Ser Ile Lys Gly Tyr Lys Gly Gly Tyr Cys Ala Ile
            20                  25                  30

Gly Gly Phe Val Cys Lys Cys Tyr
        35                  40
```